(12) United States Patent
Behkish et al.

(10) Patent No.: US 10,913,042 B2
(45) Date of Patent: Feb. 9, 2021

(54) FIXED BED RADIAL FLOW REACTOR FOR LIGHT PARAFFIN CONVERSION

(71) Applicant: ExxonMobil Research and Engineering Company, Annandale, NJ (US)

(72) Inventors: Arsam Behkish, Flemington, NJ (US); David W. Maher, Spring, TX (US); Paul F. Keusenkothen, Houston, TX (US); Jaime A. Valencia, Houston, TX (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 17 days.

(21) Appl. No.: 16/214,846

(22) Filed: Dec. 10, 2018

(65) Prior Publication Data
US 2019/0105626 A1 Apr. 11, 2019

Related U.S. Application Data

(63) Continuation of application No. 15/876,286, filed on Jan. 22, 2018, now abandoned.
(Continued)

(51) Int. Cl.
*B01J 8/02* (2006.01)
*C07C 2/76* (2006.01)
*B01J 8/04* (2006.01)

(52) U.S. Cl.
CPC ........... *B01J 8/0214* (2013.01); *B01J 8/0278* (2013.01); *B01J 8/0457* (2013.01); *B01J 8/0492* (2013.01);
(Continued)

(58) Field of Classification Search
CPC .................................. B01J 8/02; C07C 2/76
See application file for complete search history.

(56) References Cited

U.S. PATENT DOCUMENTS 3,622,504 A * 11/1971 Strum .................... C10G 5/06
95/288
3,702,886 A 11/1972 Argauer et al.
(Continued)

FOREIGN PATENT DOCUMENTS

CN 103100415 B 6/2015
CN 105618127 B 1/2018
(Continued)

OTHER PUBLICATIONS

Progress in catalytic naphtha reforming process: A review, Applied Energy 109 (2013) pp. 79-93 (Year: 2013).*
(Continued)

*Primary Examiner* — Youngsul Jeong
(74) *Attorney, Agent, or Firm* — Liza Negron

(57) ABSTRACT

Systems and methods are provided for conversion of light paraffinic gases to form liquid products in a process performed in a fixed bed radial-flow reactor. The light paraffins can correspond to $C_{3+}$ paraffins. Examples of liquid products that can be formed include $C_6$-$C_{12}$ aromatics, such as benzene, toluene, and xylene. The fixed bed radial-flow reactor can allow for improved control over the reaction conditions for paraffin conversion in spite of the fixed bed nature of the reactor. This can allow the process to operate with improved efficiency while reducing or minimizing the complexity of operation relative to non-fixed bed reactor systems.

12 Claims, 6 Drawing Sheets

Related U.S. Application Data

(60) Provisional application No. 62/459,829, filed on Feb. 16, 2017.

(52) U.S. Cl.
CPC ....... *C07C 2/76* (2013.01); *B01J 2208/00106* (2013.01); *B01J 2208/00176* (2013.01); *B01J 2208/00884* (2013.01); *B01J 2208/02* (2013.01); *B01J 2219/00038* (2013.01); *C07C 2521/04* (2013.01); *C07C 2521/08* (2013.01); *C07C 2529/40* (2013.01)

(56) References Cited

U.S. PATENT DOCUMENTS

| | | | |
|---|---|---|---|
| 3,927,987 | A | 12/1975 | Winter, III et al. |
| 3,960,978 | A | 6/1976 | Givens et al. |
| 3,978,150 | A | 8/1976 | McWilliams, Jr. |
| 3,996,014 | A | 12/1976 | Muller et al. |
| 4,021,502 | A | 5/1977 | Plank et al. |
| 4,080,395 | A | 3/1978 | Butter |
| 4,110,081 | A | 8/1978 | Millar et al. |
| 4,150,062 | A | 4/1979 | Garwood et al. |
| 4,227,992 | A | 10/1980 | Garwood et al. |
| 4,456,781 | A | 6/1984 | Marsh et al. |
| 4,636,483 | A * | 1/1987 | Kjell ............... B01J 29/44 502/61 |
| 5,130,106 | A | 7/1992 | Koves et al. |
| 5,919,722 | A | 7/1999 | Verduijn et al. |
| 5,936,135 | A | 8/1999 | Choudhary et al. |
| 5,998,686 | A | 12/1999 | Clem et al. |
| 6,074,975 | A | 6/2000 | Yao et al. |
| 7,659,437 | B2 | 2/2010 | Iaccino et al. |
| 7,759,535 | B2 | 7/2010 | Iaccino et al. |
| 7,772,447 | B2 | 8/2010 | Iaccino et al. |
| 8,835,706 | B2 | 9/2014 | Iyer et al. |
| 8,841,227 | B2 | 9/2014 | Sangar et al. |
| 8,981,169 | B2 | 3/2015 | Iaccino et al. |
| 2006/0135831 | A1 | 6/2006 | Butler et al. |
| 2008/0027254 | A1 | 1/2008 | Zhou et al. |
| 2009/0209794 | A1 | 8/2009 | Lauritzen et al. |
| 2011/0054232 | A1 | 3/2011 | Sangar et al. |
| 2011/0124933 | A1 | 5/2011 | Kiesslich et al. |
| 2011/0257452 | A1 | 10/2011 | Khabashesku et al. |
| 2011/0270002 | A1 | 11/2011 | Yanagawa et al. |
| 2012/0079938 | A1 * | 4/2012 | Celik ............... B01D 53/0462 95/95 |
| 2012/0136191 | A1 | 5/2012 | Stitt et al. |
| 2013/0116493 | A1 * | 5/2013 | Liu ............... C07C 2/76 585/417 |
| 2014/0369892 | A1 | 12/2014 | Zhou et al. |
| 2015/0158789 | A1 | 6/2015 | Keusenkothen et al. |

FOREIGN PATENT DOCUMENTS

| | | |
|---|---|---|
| EP | 0088494 A1 | 9/1983 |
| WO | 2009061760 A1 | 5/2009 |
| WO | 2017/052856 A1 | 3/2017 |

OTHER PUBLICATIONS

Composition of naphtha from fluid catalytic cracking, 1952, Industrial and Engineering Chemistry, vol. 44, No. 5, pp. 1142-1146 (Year: 1952).*

Mravec et al., "Synthesis of the zeolite ZSM-5 using seed crystals", Chem. Papers, 45, pp. 27-33 (1991).

Long et al., "Effect of lanthanum and phosphorous on the aromatization activity of Zn/ZSM-5 in FCC gasoline upgrading", Microporous and Mesoporous Materials 198 (2014) 29-34.

Aritani et al., "Methane dehydroaromatization over Mo-modified H-MFI for gas to liquid catalysts", J. of Environmental Sciences 21 (2009) 736-740.

Chen et al., "M2 Forming—A Process for Aromatization of Light Hydocarbons", Ind. Eng. Chem. Process Des. Dev. 1986, 25, 151-155.

Liu et al., "Efficient Conversion of Methane to Aromatics by Coupling Methylation Reaction", ACS Catal. 2016, 6, 5366-5370.

Lermer et al., "Synthesis and structure refinement of ZSM-5 single crystals", Zeolites, 1985, vol. 5, May, 131-134.

Tabak et al., "Production of Synthetic Gasoline and Diesel Fuel From Non-Petroleum Resources", p. 293-299, 1986 https://web.anl.gov/PCS/acsfuel/preprint%20archive/Files/31_2_NEW%20YORK_04-86_0293.pdf accessed on Sep. 21, 2018.

Zhou et al., "Synthesis of mesoporous ZSM-5 zeolite crystals by conventional hydrothermal treatment", Electronic Supplementary Material for RSC Advances, Royal Society of Chemistry 2013.

Xu et al., "Performance of a binder-free, spherical-shaped Mo/HZSM-5 catalyst in the non-oxidative CH4 dehydroaromatization in fixed- and fluidized-bed reactors under periodic CH4—H2 switch opera", Chemical Engineering and Processing, 2013, vol. 72, pp. 90-102.

The International Search Report and Written Opinion of PCT/US2018/014626 dated Apr. 18, 2018.

* cited by examiner

FIXED BED RADIAL FLOW REACTOR FOR LIGHT PARAFFIN CONVERSION

CROSS-REFERENCE TO RELATED APPLICATIONS

This application is a continuation application filed under 37 C.F.R. 1.53(b) of parent U.S. patent application Ser. No. 15/876,286 filed on Jan. 22, 2018, the entirety of which is hereby incorporated herein by reference, which claims priority to U.S. Provisional Application Ser. No. 62/459,829 filed Feb. 16, 2017, also herein incorporated by reference in its entirety.

FIELD

This invention relates to reactors, associated reactor systems, and processes for conversion of paraffin-containing streams to aromatics.

BACKGROUND

Oil extraction sites for withdrawal of petroleum from a mineral reservoir can typically produce a mixture of gas and liquid phase products. The liquid phase products from the mineral reservoir can typically be stored in tanks and/or diverted into a pipeline system to allow for further processing at a central location. While the liquid phase petroleum product is often the primary desired target, the gas phase product (such as raw natural gas) can also include substantial carbon content. Unfortunately, transportation of such gas phase products can present substantial difficulties which may make it cost prohibitive to attempt to transport the gas phase products (or at least portions of the gas phase products) for further processing. In situations where transport of gas phase products is not feasible, the resulting gas phase products may be burned for fuel value and/or flared.

U.S. Patent Application Publication 2015/0158789 describes an integrated system and corresponding method for processing $C_3+$ gas phase products generated at an extraction site to convert the gas phase products to liquid products. The liquid products can then be transported for further processing along with the extracted liquid phase products.

SUMMARY

In various aspects, a fixed bed radial flow reactor is provided. The reactor can include an outer annular volume defined by an interior of a reactor wall and an exterior of a gas-permeable catalyst bed wall, the interior of the reactor wall defining an outer annular radius R1. The reactor can further include a central volume defined by the interior of a gas-permeable central column wall and a column cap, the interior of the central column wall defining a column radius R3. The reactor can further include an inner annular volume defined by an interior of the catalyst bed wall, an exterior of the central column wall, an inner annular top, and an inner annular bottom, the interior of the catalyst bed wall defining an inner annular radius R2. The inner annular volume can comprise a catalyst bed. The inner annular volume can be in direct fluid communication with the outer annular volume through the catalyst bed wall. The inner annular volume can be in direct fluid communication with the central volume through the central column. The reactor can further include a plurality of catalyst particles in the catalyst bed, the catalyst particles comprising an equivalent particle diameter $d_{P,e}$. The reactor can further include a first reactor opening and a second reactor opening, the first reactor opening being in fluid communication with the outer annular volume, the second reactor opening being in fluid communication with the central volume. The outer annular radius R1, inner annular radius R2, and the equivalent particle diameter $d_{P,e}$ can satisfy the relationship $C^*d_{P,e} \leq R1-R2 \leq D^*d_{P,e}$, where C is at least 30 and D is 300 or less. The inner annular radius R2, the column radius R3, and the equivalent particle diameter $d_{P,e}$ can satisfy the relationship $A^*d_{P,e} \leq R2-R3 \leq B^*d_{P,e}$, where A is at least 100 and B is 600 or less.

In some aspects, the first reactor opening can comprises a reactor inlet and/or the second reactor opening can comprise a reactor outlet. In some aspects, the catalyst bed wall can comprise a perforated wall, a catalyst bed screen, or a combination thereof. Optionally, the inner annular volume can further comprise gas phase hydrocarbons, at least 5 vol % of the gas phase hydrocarbons comprising $C_{3+}$ paraffins relative to a weight of the gas phase hydrocarbons, the at least 5 vol % of $C_{3+}$ paraffins optionally comprising at least 5 vol % of $C_3$-$C_6$ paraffins or $C_3$-$C_4$ paraffins.

In various aspects, a method for processing a paraffin-containing feed is provided. The method can include exposing a feed to a catalyst in a fixed bed radial flow reactor, such as the reactor described above. The feed can comprise about 30 vol % to about 70 vol % of $C_{3+}$ paraffins. The feed can be exposed to one or more fixed beds of a conversion catalyst in one or more such fixed bed radial flow reactors to form a conversion effluent comprising $C_6$-$C_{12}$ aromatics (or $C_6$-$C_9$ aromatics). A combined pressure drop across the one or more fixed beds can be less than about 100 kPag (or less than about 50 kPag).

In some aspects, the feed can be exposed to the conversion catalyst at a temperature of about 450° C. to about 650° C., a pressure in the one or more fixed catalyst beds comprising at least about 200 kPa-a (or at least about 300 kPa-a, or about 200 kPa-a to about 450 kPa-a), and a WHSV of about 0.1 $hr^{-1}$ to about 4.0 $hr^{-1}$. Optionally, at least a portion of the feed can be heated after exposure of the feed to a first catalyst bed of the one or more catalyst beds and prior to exposure of the feed to a second catalyst bed of the one or more catalyst beds. In some aspects, a temperature drop across a first catalyst bed of the one or more catalyst beds can be about 125° C. or less, or about 100° C. or less.

In some aspects, the method can further include separating $C_{3+}$ paraffins from a natural gas feedstock to form at least a fraction comprising $C_{3+}$ paraffins and mixing at least a portion of the fraction separated $C_{3+}$ paraffins with a gas comprising methane, ethane, or a combination thereof to form an enriched feedstock. In such aspects, at least a portion of the enriched feedstock can be exposed to the one or more fixed beds of conversion catalyst. The gas comprising methane, ethane, or a combination thereof can optionally comprise a portion of the natural gas feedstock, a fraction separated from the natural gas feedstock, or a combination thereof.

Optionally, the about 30 vol % to about 70 vol % $C_{3+}$ paraffins can comprise about 30 vol % to about 70 vol % of $C_3$-$C_6$ paraffins or $C_3$-$C_4$ paraffins.

In some aspects, the method can further comprise separating the conversion effluent to form a fraction comprising $C_6$-$C_{12}$ aromatics (or $C_6$-$C_9$ aromatics), and combining at least a portion of the fraction comprising $C_6$-$C_{12}$ aromatics with a hydrocarbon liquid.

In various aspects, A can be at least 200, or at least 300, and/or B can be 500 or less, or 400 or less, or a combination thereof and/or C can be at least 50 and/or D can be less than 200, or less than 150, or c) a combination of a) and b). In some aspects, the equivalent particle diameter can be about 0.2 cm to about 4.0 cm, or about 1.0 cm to about 3.0 cm.

In some aspects, i) the catalyst particles can comprise at least one medium pore molecular sieve having a Constraint Index of 2-12; ii) the catalyst particles can comprise ZSM-5, ZSM-11, ZSM-12, ZSM-22, ZSM-23, ZSM-35, ZSM-48, MCM-22, MCM-49, or a combination thereof; iii) the catalyst particles can comprise 0.1 wt % to 5.0 wt % of a metal from Groups 3-13 of the periodic table relative to a weight of the catalyst particles, the metal optionally comprising Ga, In, or a combination thereof; or d) a combination of a) and/or b) and/or c).

DETAILED DESCRIPTION

Figure 1:
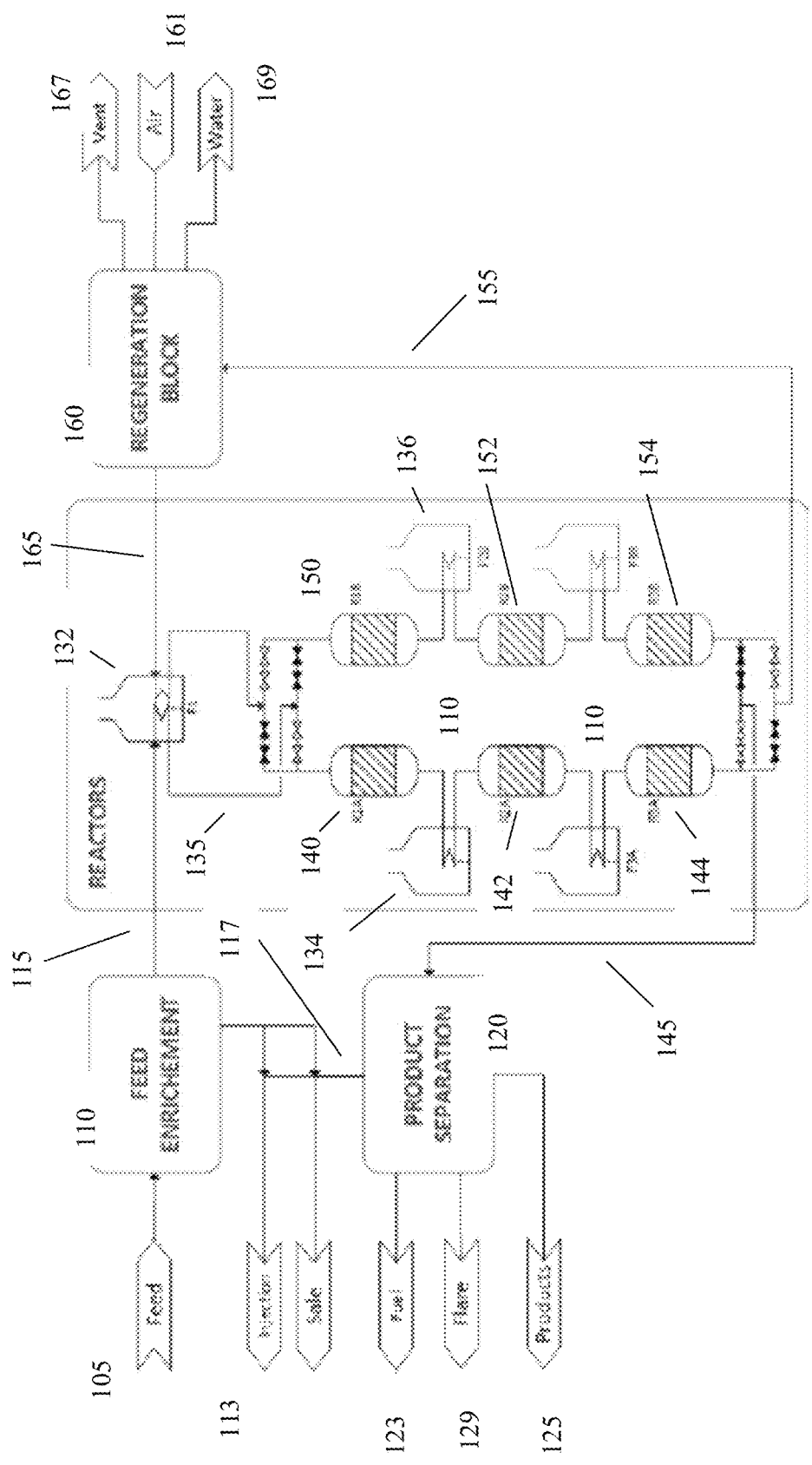
FIG. 1 shows a process flow for processing gas phase products from an extraction site.

In various aspects, systems and methods are provided for conversion of light paraffinic gases to form liquid products in a process performed in a fixed bed radial-flow reactor. The light paraffins can correspond to $C_{3+}$ paraffins, or $C_3$-$C_9$ paraffins, or $C_3$-$C_6$ paraffins, or $C_3$-$C_4$ paraffins. Examples of liquid products that can be formed include $C_6$-$C_{12}$ aromatics, or $C_6$-$C_9$ aromatics, such as benzene, toluene, and xylene. Performing the paraffin conversion in a fixed bed reactor can be beneficial for simplifying the operation of the reactor. This can reduce or minimize the amount of operator intervention that is required to maintain the reactor in a desired operational state. However, conventional fixed bed processes for conversion of paraffins to liquid products can present difficulties in maintaining the reaction conditions within a reactor in a desired pressure and/or temperature range. The fixed bed radial-flow reactor described herein can allow for unexpectedly improved control over the reaction conditions for paraffin conversion in spite of the fixed bed nature of the reactor. This can allow the process to operate with improved efficiency while reducing or minimizing the complexity of operation relative to non-fixed bed reactor systems. An example of a higher complexity system that could otherwise be suitable for performing reactions as described herein is a continuous catalyst circulation reactor.

Raw natural gas recovered at a well-head usually contains impurities and contaminants including water vapor, hydrogen sulfide, carbon dioxide, nitrogen, and other compounds. However, most techniques for converting light hydrocarbons into aromatic, or heavy hydrocarbons, utilize a feedstock of purified hydrocarbons having 2 to 5 carbon atoms per molecule. Some of the methods for purification may include hydrogenation, dehydrogenation, sulfur, and acid gas removal techniques, among other processes, to remove the aforementioned impurities and contaminants. Thus, the purified hydrocarbon feed utilized in the conventional production of aromatic hydrocarbons usually includes propane, propylene, butanes, butylenes, with unsaturated compounds being preferred in many processes. Further, specific hydrocarbon reactants can be separated from the purified stream by fractionation. The resulting gaseous hydrocarbons may then be recycled or transported for further processing or commercialization.

However, in remote locations, the appropriate infrastructures may not exist to purify and fractionate the raw natural gas before it can be used. Thus, the recovery of raw natural gas may not outweigh the cost to implement the necessary facilities to remove, purify, and transport the natural gas from remote locations. Thus, the raw natural gas may be burned or flared as a byproduct of oil production. Unfortunately, flaring wastes the energy content of the gaseous hydrocarbons. Furthermore, flaring can pose a hazard to human health due to constituents that may be present in the natural gas, such as sulfur compounds.

In various aspects, a raw natural gas feed (or other feed comprising $C_{3+}$ paraffins) can be processed to convert $C_{3+}$ paraffins into compounds that are liquids at standard temperature and pressure, such as aromatic compounds. The resulting converted products can then be suitable for transport in the same manner as other liquid products generated at an extraction site. The conversion can unexpectedly be performed with a reduced or minimized amount of pressure drop by performing the conversion reaction in one or more fixed bed radial-flow reactors, where the geometry of the reactor has a specified relationship to the equivalent particle diameter of the catalyst particles in the reactor(s).

Definitions

The term "aromatic hydrocarbons" refers to molecules containing one or more aromatic rings. Examples of aromatic hydrocarbons are benzene, toluene, xylenes, naphthalene, and methylnaphthalenes.

The term "aromatic" refers to unsaturated compounds with at least one closed ring of at least 6 atoms, with all of the ring atoms being co-planar or almost co-planar and covalently linked, and with all of the ring atoms being part of a mesomeric system. As used herein, when the "aromatic" substituent is monocyclic, it preferably contains 6 ring atoms, and when the "aromatic" substituent is polycyclic, it preferably contains 10 ring atoms contained in fused rings.

The term "$C_n$" hydrocarbon refers to a hydrocarbon with "n" carbon atoms, and "$C_n$-$C_m$ hydrocarbons" represents hydrocarbons having between "n" and "m" carbon atoms.

The term "catalyst" refers to a material, which under certain conditions of temperature or pressure increases the rate of specific chemical reactions. A catalyst may also be a material that performs as a physisorbent or chemisorbent for specific components of the feed stream.

The term "chain length" may broadly refer to a number of atoms forming and/or making a backbone and/or structure of a molecule and/or compound, such as carbon atoms for a hydrocarbon.

The term "chemical reaction" refers to any process including the breaking or making of chemical bonds including a dissociation, recombination, or rearrangement of atoms.

The term "coke" refers to the solid residue remaining from the pyrolysis of hydrocarbons.

The term "crude oil" refers to hydrocarbons formed primarily of carbon and hydrogen atoms. The hydrocarbons may also include other elements, such as, but not limited to, halogens, metallic elements, nitrogen, oxygen, or sulfur.

Hydrocarbons derived from an oil-bearing formation may include, but are not limited to, kerogen, bitumen, pyrobitumen, asphaltenes, resins, oils, or combinations thereof.

The term "fixed-bed reactor" refers to a reactor containing catalyst material typically in pellet form, packed in a static bed.

The term "gas turbine" refers to a unit including a compressor, a combustion chamber, and turbine mechanically connected to the compressor, most preferably connected on a common shaft. Generally, a gas turbine uses energy from burning a fuel in the combustion chamber to power a compressor that provides an oxidant stream to the combustion chamber. This is termed the Brayton cycle. A "turbine" is used in the meaning of an expansion unit for converting of the energy of high temperature gas to rotational energy.

The term "higher hydrocarbons" refers to hydrocarbon(s) having more than one carbon atom per molecule, oxygenate having at least one carbon atom per molecule, e.g., ethane, ethylene, propane, propylene, benzene, toluene, xylenes, naphthalene, and/or methyl naphthalene; and/or organic compound(s) including at least one carbon atom and at least one non-hydrogen atom, e.g., methanol, ethanol, methylamine, and/or ethylamine.

The term "hydrocarbon" refers to an organic compound that includes primarily, if not exclusively, the elements hydrogen and carbon. Hydrocarbons may also include other elements, such as, but not limited to, halogens, metallic elements, nitrogen, oxygen, and/or sulfur. Hydrocarbons generally fall into two classes: aliphatic, or straight chain hydrocarbons, and cyclic, or closed ring hydrocarbons, including cyclic terpenes. Examples of hydrocarbon-containing materials include any form of natural gas, oil, coal, and bitumen.

The term "hydrocarbon diluent" refers to any substance containing one or more hydrocarbon compounds and/or substituted hydrocarbon compounds, which is suitable for use for diluting a hydrocarbon in the practice of the invention. For example, a tail gas stream containing hydrocarbons may be an added diluent for natural gas.

The term "hydrocarbon stream" refers to a hydrocarbon or mixtures of hydrocarbons that are gases or liquids. For example, hydrocarbon fluids may include a hydrocarbon or mixtures of hydrocarbons that are gases or liquids at formation conditions, at processing conditions or at ambient conditions (15° C. and 1 atm pressure). Hydrocarbon fluids may include, for example, oil, natural gas, coalbed methane, shale oil, pyrolysis oil, pyrolysis gas, a pyrolysis product of coal, and other hydrocarbons that are in a gaseous or liquid state The term "light hydrocarbons" refer to hydrocarbons having carbon numbers in a range from 1 to 5.

The term "natural gas" refers to a multi-component gas obtained from a crude oil well (associated gas) or from a subterranean gas-bearing formation (non-associated gas). The composition and pressure of natural gas can vary significantly. A typical natural gas stream contains methane ($C_1$) as a significant component. Raw natural gas may also contain ethane ($C_2$), higher molecular weight hydrocarbons, acid gases (such as carbon dioxide, hydrogen sulfide, carbonyl sulfide, carbon disulfide, and mercaptans), and minor amounts of contaminants such as water, nitrogen, iron sulfide, wax, and crude oil. As used herein, natural gas includes gas resulting from the regasification of a liquefied natural gas, which has been purified to remove contaminates, such as water, acid gases, and most of the higher molecular weight hydrocarbons.

The term "high quality gas" refers to a gas that has undergone natural gas processing to separate various hydrocarbons and fluids from a raw natural gas. Also referred to as pipeline quality dry natural gas.

The term "raw natural gas" refers to a gas that is included of methane, but may also include numerous other light hydrocarbons including ethane, propane, and butanes. Higher molecular weight hydrocarbons, including pentanes, hexanes, and impurities like benzene may also be present in small amounts. Furthermore, raw natural gas may contain amounts of non-hydrocarbon impurities, such as nitrogen, hydrogen sulfide, carbon dioxide, and traces of helium, carbonyl sulfide, various mercaptans, and water.

The term "oil and gas reservoir" refers to a well or reservoir that is a subsurface zone that produces oil and/or gas and lacks communication other reservoirs. As used in the claims, "oil and gas well" and "oil and gas reservoir" are interchangeable.

The term "reservoir" refers to a formation or a portion of a formation that includes sufficient permeability and porosity to hold and transmit fluids, such as hydrocarbons or water.

Reaction System Configuration

FIG. 1 shows an example of a reactor configuration for conversion of paraffins into liquid products. The example shown in FIG. 1 includes a two-train reactor configuration including 3 stages in each train. During operation, one reactor train can be operated for conversion of paraffins to liquids while the other reactor train is undergoing a regeneration cycle. The flows to the respective reactor trains can be controlled using valves that allow paraffin-containing feed or air into the trains as appropriate to the portion of the cycle the reactor train is currently performing.

In FIG. 1, a feed 105 is introduced into a feed enrichment stage 110. Feed 105 can correspond to natural gas, raw gas, and/or another gas phase flow generated at an extraction site. The feed 105 can include a portion of $C_3$ and/or $C_4$ paraffins. The amount of combined $C_3$ and $C_4$ paraffins in feed 105 can vary depending on the nature of the extraction site. The feed enrichment stage 110 can include a condenser for separating $C_{3+}$ paraffins, such as $C_3$-$C_6$ paraffins, or $C_3$-$C_4$ paraffins, from the feed 105. Other portions of feed 105, such as methane and/or ethane, can then be blended back into the separated $C_{3+}$ to form an enriched feed 115. As an example, separation of various components from a feed 105 can include performing a separation at a predetermined dew point in the range of from −40° F. (−40° C.) to −20° F. (−28.9° C.), typically at a pressure in the range of from about 300 psia (2068 kPa) to about 2000 psia (13,800 kPa), e.g., 400 psia (2760 kPa) to 700 psia (4830 kPa).

In various aspects, the enriched feed 115 can have a $C_{3+}$ paraffin content, such as a $C_3$-$C_6$ paraffin content, or a $C_3$-$C_4$ paraffin content, of about 30 vol % to about 70 vol %, or about 30 vol % to about 60 vol %, or about 40 vol % to about 70 vol %, or about 40 vol % to about 60 vol %, or 50 vol % to 70 vol %. In some aspects, the feed (such as feed 105) can be provided to the feed enrichment stage in an amount in the range of from 10 MSCFD (290,000 $NM^3D$) to 150 MSCFD (4.3·$10^6$ $NM^3D$), or from 20 MSCFD (580,000 $NM^3D$) to 150 MSCFD (4.3·$10^6$ $NM^3D$). In some aspects, the $C_{3+}$ content of the enriched feed can correspond to a preselected $C_{3+}$ content. Having a preselected $C_{3+}$ content for the enriched feed can be beneficial for reducing variations in the amount of $C_{6+}$ products generated by the system. For example, in some aspects, the enriched feed can comprise $C_2$ hydrocarbon in an amount in the range of from 10 mole % to 35 mole % and $C_{3+}$ hydrocarbon in an amount in the range of from 40 mole % to 50 mole %. In such aspects, the amount of $C_{6+}$ product that is generated by the system can vary by no more than +/−25%.

The other carbon components in feed 105 can also be separated out for use. The $C_1$ and/or $C_2$ hydrocarbons that are not included in enriched feed 115 can be sold 113 and/or used for other purposes, while any $CO_2$ in feed 105 can be, for example, injected into the ground. The portion of the feed 105 separated out for sale can generally have characteristics that place it within established specifications for many gas pipelines, e.g., ≤12 wt. % ethane, ≤5 wt. % propane, ≤2 wt. % butanes, a Wobbe Index of from 49.01 $MJ/sm^3$ to 52.22 $MJ/sm^3$), and a heating value of from 36.07 $MJ/sm^3$ to 41.40 $MJ/sm^3$).

Enriched feed 115 can be passed into a heater 132 for heating to a desired temperature prior to conversion. Optionally, as shown in FIG. 1, heater 132 can be a common heater that also provides heat for regeneration input flow 165. The heated enriched feed 135 can then be converted in a series of reactors 140, 142, and 144. As described below, using a plurality of reactors in sequence can allow for improved control over the reaction temperature and pressure. The control over the reaction temperature can be facilitated in part by the use of intermediate heaters 134 located between reactors 140 and 142 and between reactors 142 and 144. In other aspects, any convenient number of reactors in series may be used for the conversion reaction. After performing conversion, the resulting converted effluent 145 is passed to product separation stage 120. This can allow for separation of the effluent into, for example, liquid products 125 (such as liquid products for transport along with other extracted liquid hydrocarbons), fuel 123, flare gas 129, and/or additional light ends and $CO_2$ 117 that can be sold and/or injected 113.

It is noted that reactors 150, 152, and 154 similarly correspond to a series of reactors, with intermediate heaters 136 between reactors 150 and 152 and reactors 152 and 154. The difference between reactors 140, 142, and 144 and reactors 150, 152, and 154 is the portion of the cycle being performed in each reactor train. In the example shown in FIG. 1, the reactor train corresponding to reactors 140, 142, and 144 is in the paraffin conversion portion of the cycle, while the reactor train corresponding to reactors 150, 152, and 154 is in the regeneration portion of the cycle. During regeneration, air 161 (or another oxygen-containing gas) is passed via regeneration stage 160 into regeneration input flow line 165. The regeneration input flow 165 is heated to allow for regeneration in reactors 150, 152, and 154 at elevated temperature in the presence of oxygen, so that coke can be burned off of the catalyst. The regeneration products corresponding to water and $CO_x$ can be removed, respectively, by water exhaust 169 and vent 167.

In the reactor trains shown in FIG. 1, reactor 140 is in indirect fluid communication with reactor 142, as the effluent from reactor 140 passes through an intervening process heater 134 prior to entering reactor 142. Reactor 140 is considered in direct fluid communication with process heater 134. It is noted that effluent from reactor 140 is in fluid communication with reactor 142 without passing through an intervening compressor. Although process heater 134 can increase the temperature of the effluent from reactor 140, those of skill in the art will understand that passing a feed or effluent through a process heater can typically result in a pressure drop across the heater, even though some thermal expansion may occur due to heating of the feed or effluent. Reactors 142 and 144 have a similar relationship to the fluid communication relationships between reactors 140 and 142.

Figure 2:
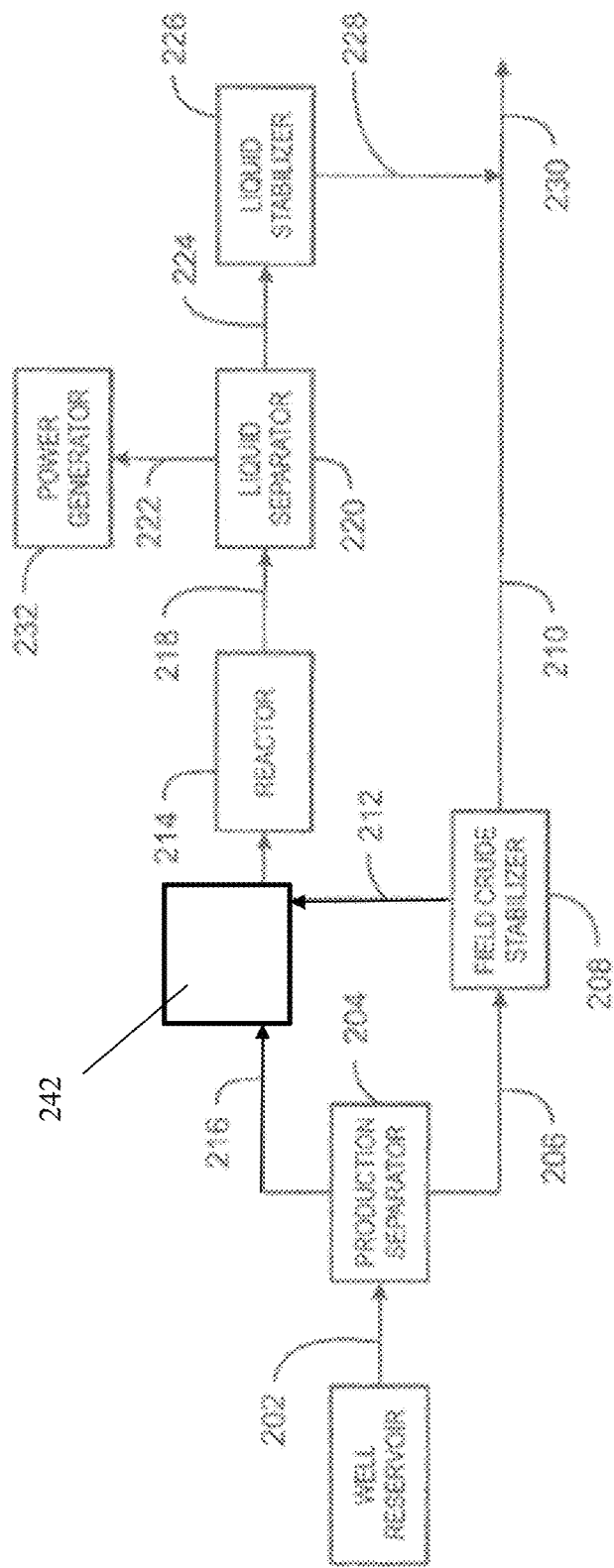
FIG. 2 shows an example of integration of fixed bed radial flow reactors into a process flow for processing gas phase products from an extraction site.

The reactor trains shown in FIG. 1 can be used as part of a larger reaction system for processing of gas phase products from an extraction site. FIG. 2 shows an example of an overall process flow that can occur at an extraction site, such as a well reservoir. The reactor train 140, 142, and 144 (as well as reactor train 150, 152, and 154), in combination with regeneration block 160, can correspond to reactor 214 in FIG. 2.

FIG. 2 is a block diagram of a system 200 for producing a higher molecular weight hydrocarbons product. As shown in FIG. 2, a raw hydrocarbon 202 may be produced from a reservoir and may flow into a production separator 204. In some embodiments, the raw hydrocarbon 202 may contain crude oil and raw natural gas along with water, trace organic compounds, trace metals, and other entrained liquids and solids. A crude oil stream 206 can be taken from the bottom of the separator 204. The crude oil stream 206 can be directed to a field crude stabilizer 208, where water, light hydrocarbons, and gas contaminants are boiled off to produce a stabilized crude oil liquid stream 210. As shown in FIG. 2, an overhead gas stream 212 from the field crude stabilizer 208 may be directed to a reactor 214.

A raw natural gas stream 216 can be taken from the top of the separator 204 and combined with the overhead gas stream 212 before being flowed into the reactor 214. In various embodiments, the stream 216 may include methane, ethane, propane, butanes, nitrogen, carbon dioxide, and hydrogen, among other components. Prior to introduction into reactor 214, the raw natural gas stream 216 and/or overhead gas stream 212 can be passed into a feed enrichment stage 242, which can optionally be similar to the feed enrichment stage 110 described in association with FIG. 1. Within the reactor 214, conversion reactions may enable the conversion of lower molecular weight hydrocarbons in the raw natural gas to higher molecular weight hydrocarbons. In some embodiments, the lower molecular weight hydrocarbons may include methane and $C_2$ to $C_{5+}$ hydrocarbons and the higher molecular weight hydrocarbons may include $C_6$ to $C_9$ aromatics. In some examples, the overhead gas stream 212 may include sulfur compounds, such as mercaptans, sulfides, and other organosulfur compounds, in addition to hydrogen sulfide ($H_2S$). The organosulfur compounds may be at least partially converted in the reactor, forming further amounts of $H_2S$.

A stream 218 containing higher molecular weight hydrocarbons may flow from the reactor 214 and into a liquid separator 220. As shown in FIG. 2, the liquid separator 220 may separate the higher molecular weight hydrocarbons containing stream 218 into a tail gas stream 222 and a liquid hydrocarbons stream 224. The product value and transportability of a hydrocarbons stream in liquid form may be enhanced since liquid hydrocarbons can achieve a higher reduction in volume than hydrocarbons in gas form. Thus, it may be more cost effective to recover the natural gas and convert it into a liquid hydrocarbons stream, instead of flaring the natural gas, since it can now be transported by methods other than pipelines.

To reduce the volatility of the liquid hydrocarbons stream 224 during transportation, the liquid hydrocarbons stream 224 may be subjected to liquid stabilization. A liquid stabilizer 226 may operate at a low pressure to remove any volatile hydrocarbons and other gaseous contaminants within the liquid hydrocarbons stream 224 to produce a stabilized liquid hydrocarbons stream 228. As shown in FIG.

2, the stabilized liquid hydrocarbons stream 228 and the stabilized crude oil liquid stream 210 may merge together to form a liquid hydrocarbons product stream 230.

If the overhead gas stream 212 used as the feed contains organosulfur compounds, $H_2S$, or both, the resulting tail gas stream 222 may be treated to reduce or remove the $H_2S$, for example, if the concentration is greater than about 10 ppm, greater than 1000 ppm, or greater than 1%, depending on the sensitivity of the environment to $SO_x$'s formed from combusting the $H_2S$. The $H_2S$ can be removed by an adsorption column, a Claus process, a counter-current separation column, or any number of other techniques. If removal of the $H_2S$ is not convenient, for example, due to the remoteness of the site, treating the combustion exhaust to remove $SO_x$'s may be performed. This could be done by passing the exhaust gas through a water scrubbing column.

The tail gas stream 222 may be utilized for on-site generation of power to turn a power generator 232, where power may be generated and used by those in remote areas with limited access to power grids. This type of distributed power generation may be attractive since it can provide electricity that may be more reliable, more efficient, and cheaper than purchasing power from a centralized utility. Distributed power generation may also allow for increased local control over an electricity supply in remote areas, as well as, possibly lowering electricity losses during transmission. Additionally, the tail gas stream 222 may be used in heat integration to supply energy to the reactor 214. In some embodiments, the power generator may include a gas turbine or combustion engine.

The block diagram of FIG. 2 is not intended to indicate that the gas system 200 is to include all of the components shown in FIG. 2. Further, any number of additional components may be included within the method of producing a higher molecular weight hydrocarbons product. The system 200 may include any suitable types of heaters, chillers, condensers, pumps, compressors, other types of separation and/or fractionation equipment, among others, including any desirable purification steps prior to introducing the gas streams 216 and 212 into reactor 214. For example, the system 200 may include a suitable device or structure for condensing at least a portion of the gas streams 216 and/or 212, e.g., a pressure expansion device, an external refrigeration system, etc., prior to introduction into the reactor 214. Condensing in this way may create a liquid stream comprising higher molecular weight hydrocarbons and a gas stream comprising methane and other light components (e.g., nitrogen, helium, carbon dioxide, etc.). The liquid stream may be vaporized and introduced into the reactor 214 as feedstock, while the gas stream may be reinjected into the ground or used for another purpose. Those of skill in the art will recognize that this technique may be utilized to variably control the composition of the tail stream, and therefore the amount of co-produced power that may be generated.

Fixed Bed Radial Flow Reactor

In various aspects, the conversion of $C_{3+}$ paraffins to liquid products can be performed using a radial flow reactor. The geometry of the radial flow reactor can be related to the size of the catalyst particles used in the reactor. The relationship between the size of the reactor and the size of the catalyst particles in the reactor can facilitate maintaining a desired temperature and pressure profile in the reactor. This can allow for unexpectedly beneficial control of reaction pressure and temperature during fixed-bed processing.

Figure 3:
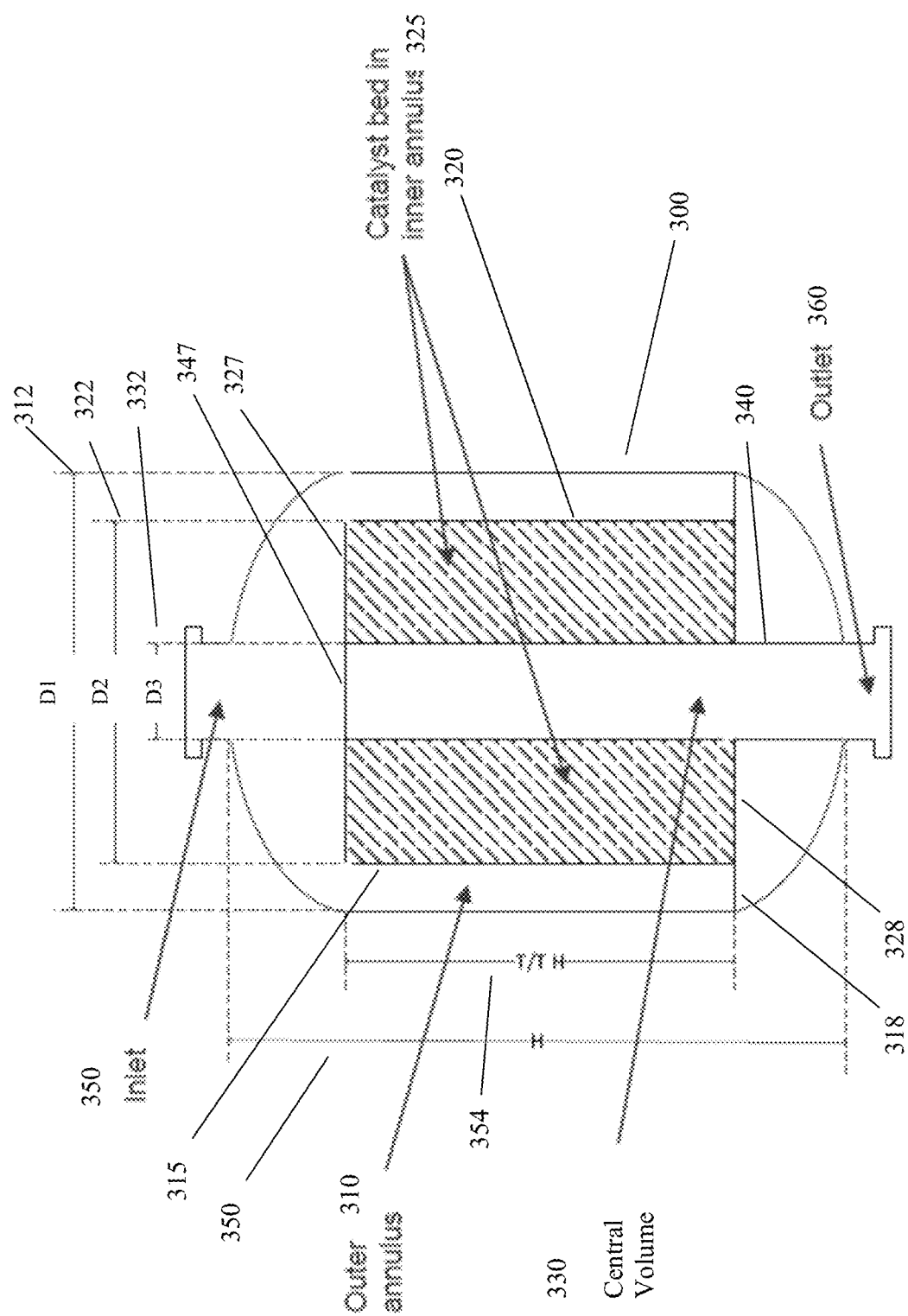
FIG. 3 schematically shows an example of a radial flow reactor.
Figure 4:
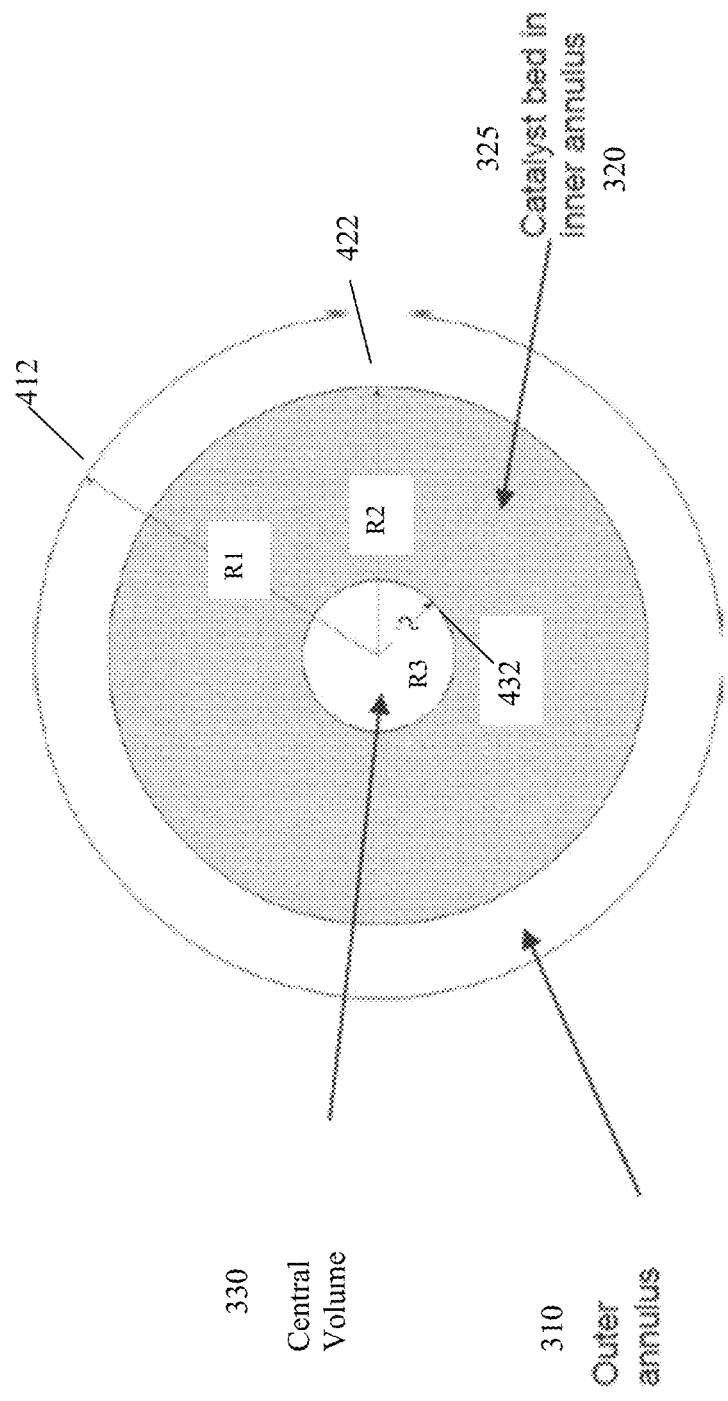
FIG. 4 shows a top view of the example of a radial flow reactor.

FIG. 3 shows the general shape of a radial flow fixed-bed reactor for conversion of paraffins to liquid products. In FIG. 3, the reactor 300 is configured to have a volume corresponding to an outer annulus 310, a volume corresponding to an inner annulus 320, and a central volume 330, such as an interior volume of a center column or standpipe 340. The outer annulus 310 is defined by the interior of the wall of reactor 300 and the exterior of a gas-permeable catalyst bed wall 315. The outer annulus bottom wall 318 further defines the outer annulus volume. In some alternative aspects, the reactor wall 300 can correspond to a plurality of walls, with the interior of the inner-most reactor wall corresponding to the wall that defines outer annulus 310. The inner annulus 320 is defined in part by the interior of the catalyst bed wall 315 and the exterior of the central column 340. The inner annulus 320 is further defined by inner annulus top wall 327 and inner annulus bottom wall 328. The central volume 330 is defined by the interior space of the center column 340. Center column 340 includes a center column cap 347. Optionally, the central volume 330 may include other structures. For example, still another central structure could be present within central volume 330, so that central volume 330 actually corresponds to another annular volume. The diameter 312, which is referred to as D1 (and radius 412, referred to as R1) correspond to the diameter (and radius) of the outer annulus. Diameter 322, which is referred to as D2 (and radius 422, referred to as R2) correspond to the diameter (and radius) of the inner annulus 320. Diameter 332, which is referred to as D3 (and radius 432, referred to as R3) correspond to the diameter (and radius) of center standpipe 330. The height 350 of the reactor can vary, depending on the catalyst bed height 354 that is desired for containing the catalyst in catalyst bed 325.

During operation, gas can enter reactor 300 via inlet 350, which is in fluid communication with outer annulus 310. It is noted that inlet 350 is not in direct fluid communication with either central volume 330 or the volume of inner annulus 320. This is due to the inner annular top wall 327 and center column cap 347. Outer annulus 310 is in fluid communication with the catalyst bed 325 in inner annulus 320 via gas-permeable catalyst bed wall 315. For example, catalyst bed wall 315 can correspond to a perforated wall, a catalyst screen, and/or any other convenient type of divider with openings that are sufficiently large to avoid a pressure drop for gas phase flow and sufficiently small to prevent passage of catalyst from catalyst bed 325 into the outer annulus 310. The wall of center column 340, such as between inner annulus top wall 327 and inner annulus bottom wall 328, can similarly be gas-permeable to allow gas flow between inner annulus 320 and central volume 330 while reducing, minimizing, or preventing movement of catalyst from catalyst bed 325 into central volume 330. The $C_{3+}$ paraffins in the feed can react in the presence of catalyst bed 325 to form conversion products, which pass through the wall of center column 340 into central volume 330. The conversion products can then exit from the reactor via the outlet 360 at the bottom of center volume 330. It is noted that outlet 360 is not in direct fluid communication with either the volume of outer annulus 310 or the volume of inner annulus 320. This is due to the inner annular bottom wall 328 and outer annular bottom wall 318. Optionally, reactor 300 could be operated with flows in the opposite directions, so that feed enters the center standpipe 330, flows outward through catalyst bed 325 in inner annulus 320, with resulting converted products end up in outer annulus 310 prior to exiting the reactor.

In order to maintain a desired level of temperature control and pressure control during the conversion reaction, the particle size for catalyst in the catalyst bed can be selected in relation to the size of the reactor (or alternatively the size of the reactor can be selected in relation to the catalyst particle size. The relationship between catalyst size and the reactor geometry can be based on an equivalent diameter of the catalyst particles. In this discussion, the equivalent diameter of a catalyst particle is defined as the diameter of a sphere that has the same external surface area as the physical shape of the catalyst. Based on this definition, the difference between the radius 422 (R2) of the inner annulus 320 and the radius 432 (R3) of the center standpipe 330 can be defined relative to the equivalent particle diameter ($d_{P,e}$) by Equation (1):

$$A*d_{P,e} \leq R2-R3 \leq B*d_{P,e} \tag{1}$$

In Equation (1), A can be at least 100, or at least 170, or at least 200, or at least 250, or at least 300, while B can be 600 or less, or 560 or less, or 500 or less, or 450 or less, or 400 or less. In other words, the difference (R2–R3) between the inner annulus radius and the center standpipe radius can be, for example, between 100 and 600 times the equivalent particle diameter, or between 170 and 560 times the equivalent particle diameter, or between 250 and 450 times the equivalent particle diameter, or between 300 and 400 times the equivalent particle diameter, or between 200 and 400 times the equivalent particle diameter, or between 300 and 500 times the equivalent particle diameter. Similarly, the difference between the radius 412 (R1) of the outer annulus 310 and the radius 422 (R2) of the inner annulus 320 can be defined relative to the equivalent particle diameter ($d_{P,e}$) by Equation (2):

$$C*d_{P,e} \leq R1-R2 \leq D*d_{P,e} \tag{2}$$

In Equation (2), C can be at least 30, or at least 50, while D can be 300 or less, or 200 or less, or 150 or less. In other words, the difference (R1–R2) between the outer annulus radius and the inner annulus radius can be, for example, between 30 and 300 times the equivalent particle diameter, or between 50 and 300 times the equivalent particle diameter, or between 50 and 200 times the equivalent particle diameter, or between 50 and 150 times the equivalent particle diameter.

Selecting a combination of equivalent catalyst particle size and reactor geometry that satisfies Equation (1) and/or Equation (2) can allow for a reduced or minimized pressure drop across the catalyst bed when operating the conversion reactor. This reduced or minimized pressure drop can allow several reactors to be operated in series while maintaining the desired pressure within a relatively narrow range. For example, a reactor train containing multiple reactors can be operated so that the pressure drop across the reactor train is less than 0.5 barg (~50 kPag), or less than 0.3 barg (~30 kPag), or less than 0.2 barg (~20 kPag), such as down to a pressure drop of 1 kPag.

An example of a suitable catalyst particle size for performing a conversion reaction can be catalyst particles that have an equivalent particle diameter of about 0.2 cm to about 4.0 cm, or about 0.5 cm to about 4.0 cm, or about 0.5 cm to about 3.0 cm, or about 1.0 cm to about 4.0 cm, or about 1.0 cm to about 3.0 cm. For example, a catalyst composed of spherical catalyst particles having an equivalent particle diameter of 2.0 cm can be suitable for use in a reactor where the difference between the catalyst standpipe radius and the inner annulus radius is between 4.0 meters and 10.0 meters, or 5.0 meters and 9.0 meters, or 6.0 meters and 8.0 meters, or 4.0 meters and 8.0 meters, or 6.0 meters and 10.0 meters. Similarly, the difference between the radius of the outer annulus and the radius of the inner annulus for such a catalyst particle size can be between 0.25 meters and 2.0 meters, or 0.25 meters and 1.5 meters, or 0.5 meters and 2.0 meters, or 0.5 meters and 1.5 meters.

In addition to controlling the pressure drop, the temperature during the conversion reaction can also be controlled based on the reactor configuration. By using a reactor train with a desired amount of catalyst in each reactor, the amount of conversion performed in each reactor can be controlled to reduce or minimize the temperature variation across each reactor. In particular, because the conversion reaction is endothermic, the temperature drop across each reactor can be controlled so that the temperature drop across the first reactor is about 200° C. or less, or about 175° C. or less, or about 150° C. or less, such as down to 50° C. or possibly still lower. Additionally or alternately, the temperature drop across the second and subsequent reactors can be about 150° C. or less, or about 125° C. or less, or about 100° C. or less.

The catalyst can include at least one metal component on an inorganic support, such as amorphous silica, or alumina. The inorganic support may be a porous material such as a micro-porous crystalline material or a meso-porous material. Additionally, suitable molecular sieves may be utilized in the present catalyst and may include at least one medium pore molecular sieve having a Constraint Index of 2-12 (as defined in U.S. Pat. No. 4,016,218). Examples of such medium pore molecular sieves include ZSM-5, ZSM-11, ZSM-12, ZSM-22, ZSM-23, ZSM-35, ZSM-48, MCM-22 and MCM-49 and mixtures and intermediates thereof. ZSM-5 is described in detail in U.S. Pat. No. 3,702,886 and Re. 29,948. ZSM-11 is described in detail in U.S. Pat. No. 3,709,979. A ZSM-5/ZSM-11 intermediate structure is described in U.S. Pat. No. 4,229,424. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

The metal component of the catalyst may be present in an amount of at least 0.1 wt. %, such as from 0.1 to 5 wt. %, of the overall catalyst. The metal component may include one or more neutral metals selected from Groups 3 to 13 of the Periodic Table of the Elements, such as Ga, In, Zn, Cu, Re, Mo, W, La, Fe, Ag, Pt, Pd, and/or one or more oxides, sulfides and/or carbides of these metals. The metal component can be provided on the catalyst in any known manner, for example by impregnation or ion exchange of the molecular sieve with a solution of a compound of the relevant metal, followed by conversion of the metal compound to the desired form, namely neutral metal, oxide, sulfide and/or carbide. Part or all of the metal may also be present in a crystalline framework of the molecular sieve.

In a preferred embodiment, a bifunctional catalyst may be selected from the group consisting of Ga and/or In-modified ZSM-5 type zeolites, such as Ga and/or In-impregnated H-ZSM-5, Ga and/or In-exchanged H-ZSM-5, H-gallosilicate of ZSM-5 type structure and H-galloaluminosilicate of ZSM-5 type structure. These zeolites can also be prepared by methods known in the prior art.

For example, the bifunctional catalyst may contain tetrahedral aluminum or gallium, which is present in the zeolite framework or lattice. The bifunctional catalyst may also contain octahedral gallium or indium, which is not present in the zeolite framework, but present in the zeolite channels in close vicinity to the zeolitic protonic acid sites that may be attributed to the presence of tetrahedral aluminum and gallium in the catalyst. The tetrahedral or framework of Al or Ga can be responsible for the acid function of the catalyst and octahedral or non-framework Ga or In may be responsible for the dehydrogenation function of the catalyst. In a preferred embodiment, the bifunctional catalyst may include H-galloaluminosilicate of ZSM-5 type structure having framework (tetrahedral) Si/Al and Si/Ga mole ratios of about 10:1 to 100:1 and 15:1 to 150:1, respectively, and non-framework (octahedral) Ga of about 0.5 to 0 wt. %.

In addition to the molecular sieve and hydrogenation component, the catalyst may be composited with other materials, which may be resistant to the temperatures and other conditions employed in the conversion reaction. Such other materials can include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst.

Additionally, inactive materials may serve as diluents to control the amount of conversion so that products can be obtained without employing other means for controlling the rate of reaction. These materials may be incorporated into naturally-occurring clays, e.g., bentonite and kaolin, to improve the crush strength of the catalyst under commercial operating conditions and function as binders or matrices for the catalyst. The relative proportions of molecular sieve and inorganic oxide matrix may vary, with the sieve content ranging from about 1 to about 90 percent by weight and more usually, particularly, when the composite is prepared in the form of beads, in the range of about 2 to about 80 weight percent of the composite.

In any embodiment, the catalysts of may comprise least one molecular sieve component and at least one dehydrogenation component. The molecular sieve component may comprise >80 wt. % to <100 wt. %, preferably 100 wt. % of said catalyst. In one or more embodiments, the catalyst can be substantially free of binder, such as an inorganic binder, or matrix material, e.g., contains ≤1 wt. % of binder or matrix material, such as, for example, ≤0.1 wt. %, based on the weight of the catalyst. In other embodiments, the molecular sieve is present in the catalyst in an amount of >80 wt. %, ≥90 wt. %, or ≥95 wt. %, or ≥98 wt. %, or ≥99 wt. %, based on the weight of the catalyst. In some embodiments, the molecular sieve is an aluminosilicate and is present in the catalyst in a range of from about 80 wt. %, or 85 wt. %, or 90 wt. %, or 95 wt. % up to about 99.9 wt. %, based on the weight of the catalyst. In a most preferred embodiment, the molecular sieve is an aluminosilicate and present in the catalyst in the amount of about 100 wt. %. The molecular sieve may consist essentially of or even consist of an aluminosilicate.

The crystalline aluminosilicate of the catalysts may have a constraint index of less than 12, preferably, in the range of about 1 to about 12. Typically, the crystalline aluminosilicate is one having a medium pore size and a Constraint Index of less than or equal to about 12. Constraint Index is defined in U.S. Pat. No. 4,016,218. Examples of suitable aluminosilicates include ZSM-5, ZSM-11, ZSM-12, ZSM-21, ZSM-22, ZSM-23, ZSM-35, ZSM-38, ZSM-48 ZSM-50, ZSM-57, and MCM-68, including mixtures and intermediates thereof such as ZSM-5/ZSM-11 admixture. ZSM-5 is described in U.S. Pat. No. 3,702,886 and Re. 29,948. ZSM-11 is described in U.S. Pat. No. 3,709,979. A ZSM-5/ZSM-11 intermediate structure is described in U.S. Pat. No. 4,229,424. ZSM-12 is described in U.S. Pat. No. 3,832,449. ZSM-21 is described U.S. Pat. No. 4,082,805. ZSM-22 is described in U.S. Pat. No. 4,556,477. ZSM-23 is described in U.S. Pat. No. 4,076,842. ZSM-35 is described in U.S. Pat. No. 4,016,245. ZSM-38 is described in U.S. Pat. No. 4,046,859. ZSM-48 is described in U.S. Pat. No. 4,234,231. ZSM-50 is described in U.S. Pat. No. 4,640,826. ZSM-57 is described in U.S. Pat. No. 4,873,067. TEA-Mordenite is described in U.S. Pat. Nos. 3,766,093 and 3,894,104. MCM-68 is described in U.S. Pat. No. 6,049,018.

The aluminosilicate's silica-to-alumina (Si:Al$_2$) atomic ratio may be typically ≥2 molar, e.g., in the range of 10 to 300 molar, or in the range of from 5 to 100 molar. The silica-to-alumina ratio, Si:Al$_2$, is meant to represent the Si:Al$_2$ atomic ratio in the rigid anionic framework of the crystalline aluminosilicate. In other words, aluminum in (i) any matrix or binder or (ii) in cationic or other form within the crystalline aluminosilicate's channels is excluded from the Si:Al$_2$ atomic ratio. Aluminosilicates having a higher silica-to-alumina ratio can be utilized when a lower catalyst acidity is desired, e.g., in the range of from 44 to 100 molar, such as from 50 to 80 molar, or 55 to 75 molar.

In one or more embodiments, the crystalline aluminosilicate has a constraint index in the range of about 1 to 12 and is selected from the group consisting of a MCM-22 family material, ZSM-5, ZSM-11, ZSM-12, ZSM-21, ZSM-22, ZSM-23, ZSM-35, ZSM-38, ZSM-48, ZSM-50, ZSM-57, MCM-68 and mixtures of two or more thereof. Preferably, the aluminosilicate is ZSM-11 or H-ZSM-11 (the acidic form of ZSM-11), and more preferably, the aluminosilicate is ZSM-5 or H-ZSM-5 (the acidic form of ZSM-5).

In certain aspects, the molecular sieve has a relatively small crystal size, e.g., small crystal ZSM-5, meaning ZSM-5 has a crystal size≤0.05 μm, such as in the range of 0.02 μm to 0.05 μm. Small crystal ZSM-5 and the method for determining molecular sieve crystal sizes are disclosed in U.S. Pat. No. 6,670,517, which is incorporated by reference herein in its entirety.

In other aspects, the crystalline aluminosilicate comprises at least one molecular sieve of the MCM-22 family, e.g., MCM-22 alone or in combination with other aluminosilicates, specified above, or other MCM-22 family materials. Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), and ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697) and mixtures of two or more thereof. Related aluminosilicates to be included in the MCM-22 family are UZM-8 (described in U.S. Pat. No. 6,756,030) and UZM-8HS (described in U.S. Pat. No. 7,713,513), both of which are also suitable for use as the molecular sieve component.

In one or more embodiments, the molecular sieve may be one that is in hydrogen form, e.g., one that has been synthesized in the alkali metal form, but is then converted from the alkali to the hydrogen form and has hydrogen ions, e.g., acidic.

The dehydrogenation component comprises at least one element from Group 5 to 15 of the Periodic Chart. In one or more embodiments, the element is a metal. Preferably, the catalyst comprise at least one first metal. The first metal is selected from the group consisting of and includes one or more of zinc, gallium, copper, silver, tin, iron, cobalt, nickel, gold, manganese, chromium, molybdenum, tungsten, and mixtures of two or more thereof. Preferably, the first metal is zinc or gallium.

In one or more embodiments, the dehydrogenation component of the catalysts of this invention further comprises at least one second metal in addition to the first metal. The second metal is different from the first metal. The second metal is selected from the group consisting of and includes one or more of phosphorus, platinum, palladium, lanthanum rhenium, and mixtures of two or more thereof. Preferably, the second metal is phosphorous.

The catalyst contains at least about 0.005 wt. % of the first metal, or in the range from about 0.005 wt. % to about 4.0 wt. % of said first metal, or from about 0.01 wt. % to about 3.0 wt. % of said first metal, based on the weight of said catalyst. When the second metal is present, the catalyst contains in the range from 0 wt. % to about 5.0 wt. % of the second metal, or from about 0.005 wt. % to about 4.0 wt. % of said second metal, or from about 0.01 wt. % to about 3.0 wt. % of said second metal, based on the weight of the catalyst.

Not being bound by any theory, it is believed that the higher catalyst activity provided by the increased molecular sieve (preferably, aluminosilicate) content is modulated by the presence of the first metal and optionally, the second metal, leading to increased cycle length when the catalyst is used in a process for conversion of a light paraffinic hydrocarbon feedstock in a fixed bed reactor.

An inorganic binder or matrix material may be used, e.g., to make the catalyst more resistant to the temperatures and other conditions employed in the process for conversion. The amount of such inorganic binder or matrix material is set forth above.

The inorganic binder or matrix material may include clays and/or inorganic oxides. Such inorganic binders include alumina, silica, silica-alumina, titania, zirconia, magnesia, tungsten oxide, ceria, niobia, and mixtures of two or more thereof. The matrix component may include naturally occurring materials and/or materials in the form of gelatinous precipitates or gels including mixtures of silica and metal oxides. Clays may also be included with the oxide type binders to modify the mechanical properties of the catalyst or to assist in its manufacture. Alternatively, or in addition, the inorganic binder or matrix material may include one or more substantially inactive materials. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve thermal and strength properties (e.g., crush strength) of the catalyst under catalytic conversion conditions. The binder or matrix material may include active materials, such as synthetic or naturally occurring aluminosilicate.

The catalyst, preferably a catalyst having a molecular sieve component comprises >80 wt. % to <100 wt. % of said catalyst and a dehydrogenation component comprised of a first metal and an optional second metal, provides ≤a 5% reduction in yield of said aromatic hydrocarbon after a time-on-stream of ≤50 hours.

In one or more embodiments, the catalyst produces ≤a 5% reduction, or a 7% reduction, preferably ≤a 10% reduction, in the yield of the aromatic hydrocarbon after the time-on-stream of the catalyst is at least 20 hours, or at least 50 hours, preferably at least 100 hours under conversion conditions of a temperature in the range of about 450° C. to about 750° C., a pressure in the range of from about 35 kPa to about 1480 kPa and a WHSV from about 0.1 to about 20 hr$^{-1}$.

In a preferred embodiment, the catalyst of this invention is a catalyst for producing aromatic hydrocarbon comprising: (a) from >80 wt. % to <100 wt. % of a crystalline aluminosilicate which comprises ZSM-5 or ZSM-11, based on the weight of said catalyst; (b) about 0.005 wt. % to about 5.0 wt. % of a first metal, based on the weight of said catalyst, and (c) 0 wt. % to about 5.0 wt. % of a second metal, based on the weight of said catalyst, wherein said catalyst has ≤a 5% reduction in yield of aromatic hydrocarbon after an average time-on-stream in said reaction zone of at least 50 hours in a process for producing aromatic hydrocarbon which includes converting ≥1 wt. % of a $C_2$-non-aromatic hydrocarbon in the presence of said catalyst to a product comprising ≥1 wt. % of aromatic hydrocarbon under conversion conditions that include a temperature in the range of about 450° C. to about 750° C., a pressure in the range of from about 35 kPa to about 1480 kPa and a WHSV from about 0.1 to about 20 hr$^{-1}$. In one or more embodiments, the first metal, optional second metal and inorganic binder are as set forth above. The catalysts of this invention are made by any one of the methods disclosed hereinafter.

A method of making one or more catalysts for use in the process may comprise the first step of providing a molecular sieve, preferably a crystalline aluminosilicate, which has a constraint index of less than or equal to about 12, preferably in the range of about 1 to about 12, more preferably, a crystalline aluminosilicate comprising ZSM-5 or ZSM-11. In a contacting step, the molecular sieve is contacted with a source of a first metal and optionally a source of a second metal under conditions sufficient to deposit said first metal and said optional second metal on the molecular sieve and to form a metal-containing molecular sieve.

If both metals are used, the first metal is different from the second metal. The first metal is selected from the group consisting of zinc, gallium, copper, silver, tin, iron, cobalt, nickel, gold, manganese, chromium, molybdenum, indium, tungsten, and mixtures of two or more thereof. The second metal is selected from the group consisting of phosphorus, platinum, palladium, lanthanum rhenium, and mixtures of two or more thereof.

The first metal and the optional second metal may be deposited on the crystalline aluminosilicate, by any suitable method, e.g., by impregnating the first metal and optionally the second metal onto the external surface of the molecular sieve, preferably the crystalline aluminosilicate. The first metal and optionally the second metal may be dissolved in a liquid carrier, for example an aqueous or organic carrier, mixed with the catalyst, and then dried by evaporation or vacuum distillation. This method may be termed "impregnation". Other conventional methods may be utilized to deposit the first metal and the optional second metal onto the molecular sieve, preferably the crystalline aluminosilicate, such as for example, by the incipient wetness method, and the invention is not limited to any one specific method. Non-limiting examples of the conditions effective to deposit the first metal and optionally the second metal on the molecular sieve, preferably the crystalline aluminosilicate, are set forth in Example 3.

When the first metal is zinc, non-limiting suitable sources of zinc are selected from the group consisting of zinc nitrate, zinc titanate, zinc silicate, zinc borate, zinc fluorosilicate, zinc fluorotitanate, zinc molybdate, zinc chromate, zinc tungstate, zinc zirconate, zinc chromite, zinc aluminate, zinc phosphate, zinc acetate dihydrate, diethyl zinc, zinc 2-ethylhexanoate, and mixtures of two or more thereof.

When the second metal is lanthanum, non-limiting suitable sources of lanthanum include a lanthanum salt, a lanthanum nitrate, or a mixture thereof.

Fixed Bed Processing Conditions

In various aspects, a paraffin conversion reaction can be performed by exposing a paraffin-containing feed to a conversion catalyst in the presence of hydrogen at suitable conversion conditions. The feed can correspond to a feed containing about 30 vol % to 70 vol % of $C_{3+}$ paraffins, or 30 vol % to 70 vol % $C_3$-$C_6$ paraffins, or 30 vol % to 70 vol % $C_3$-$C_4$ paraffins. It has been determined that reaction conditions including a temperature of about 500° C. to about 650° C. (or about 550° C. to 650° C., or about 525° C. to about 625° C., or about 550° C. to about 600° C.), a total pressure of about 100 kPa-a to about 525 kPa-a (or about 200 kPa-a to about 525 kPa-a, or about 200 kPa-a to about 450 kPag, or about 300 kPa-a to about 450 kPa-a, or about 200 kPa-a to about 350 kPa-a), and a weight hour space velocity (WHSV) of about 0.1 $hr^{-1}$ to about 4.0 $hr^{-1}$, or about 0.5 $hr^{-1}$ to about 2.0 $hr^{-1}$, can be beneficial for performing paraffin conversion to liquid (aromatic) products. Additionally, maintaining a partial pressure of hydrogen within the reactor can be beneficial for reducing or minimizing the formation of coke on the catalyst. Additionally or alternately, if the reaction temperature drops below 450° C., or alternatively below 475° C., the reaction rate of the desired paraffin-to-aromatics conversion reaction can drop significantly, while increasing the temperature above about 650° C. can lead to increases in the catalyst coking rate.

In order to maintain a desired level of control over the temperature during the conversion reaction, the catalyst can be distributed across multiple reactors in a reactor train. For example, a first reactor can include 5 wt % to 15 wt % of the conversion catalyst, a second reactor can include 15 wt % to 30 wt % of the conversion catalyst, and the third reactor can include the remaining balance of the catalyst. During operation, the feed can be initially heated to a desired temperature, such as at least 550° C., or at least 600° C., such as up to about 650° C. The feed can then be passed into a first reactor. It is noted that the $C_{4+}$ components in a feed for conversion can react more rapidly than the $C_3$ components. By providing only 5 wt % to 15 wt % of the catalyst in the first reactor, such as 5 wt % to 10 wt %, or 10 wt % to 15 wt %, a portion of the $C_{4+}$ components in the feed can be reacted, while leaving some $C_{4+}$ components and a majority of $C_3$ components unreacted. This can reduce or minimize the temperature drop across the first reactor. After the first reactor, an intermediate heater can be used to return the temperature of the partially converted feed to a desired temperature, such as at least 550° C. or at least 575° C., such as up to about 600° C. or up to about 625° C. The second reactor can then include another portion of the catalyst that is sufficient for reacting the remaining $C_{4+}$ components in the feed under the conversion conditions. Again, the twice partially converted feed can be returned to a desired temperature, such as at least 550° C. or at least 575° C., such as up to about 600° C. or up to about 625° C., using another intermediate heater. The twice partially converted feed can then be exposed to the remaining catalyst in a third (possibly final) reactor to complete a desired amount of conversion on the $C_3$ components in the feed. The effluent from the third reactor can then be passed into a separation stage, where liquid aromatic products ($C_{6+}$) and/or other liquid products can be separated from light gases ($C_1$-$C_3$ and $H_2$) in the effluent.

After processing for a period of time, the catalyst in the reactor train can accumulate coke, which can result in a loss in catalyst activity. The reactor train can then be switched to a regeneration mode to remove coke from the catalyst. After optionally purging the catalyst train of any remaining hydrocarbons, diluted air having an oxygen content of about 0.5 vol % to about 6 vol % (or another oxygen-containing gas) can be heated to a temperature of between 325° C. to 600° C. and introduced into the reaction train. The heated oxidizing environment can allow for combustion of coke to form carbon oxides and some water, which can then be vented and/or recovered from the reaction train.

Example 1—Modeling of Temperature During Conversion Reaction

Figure 5:
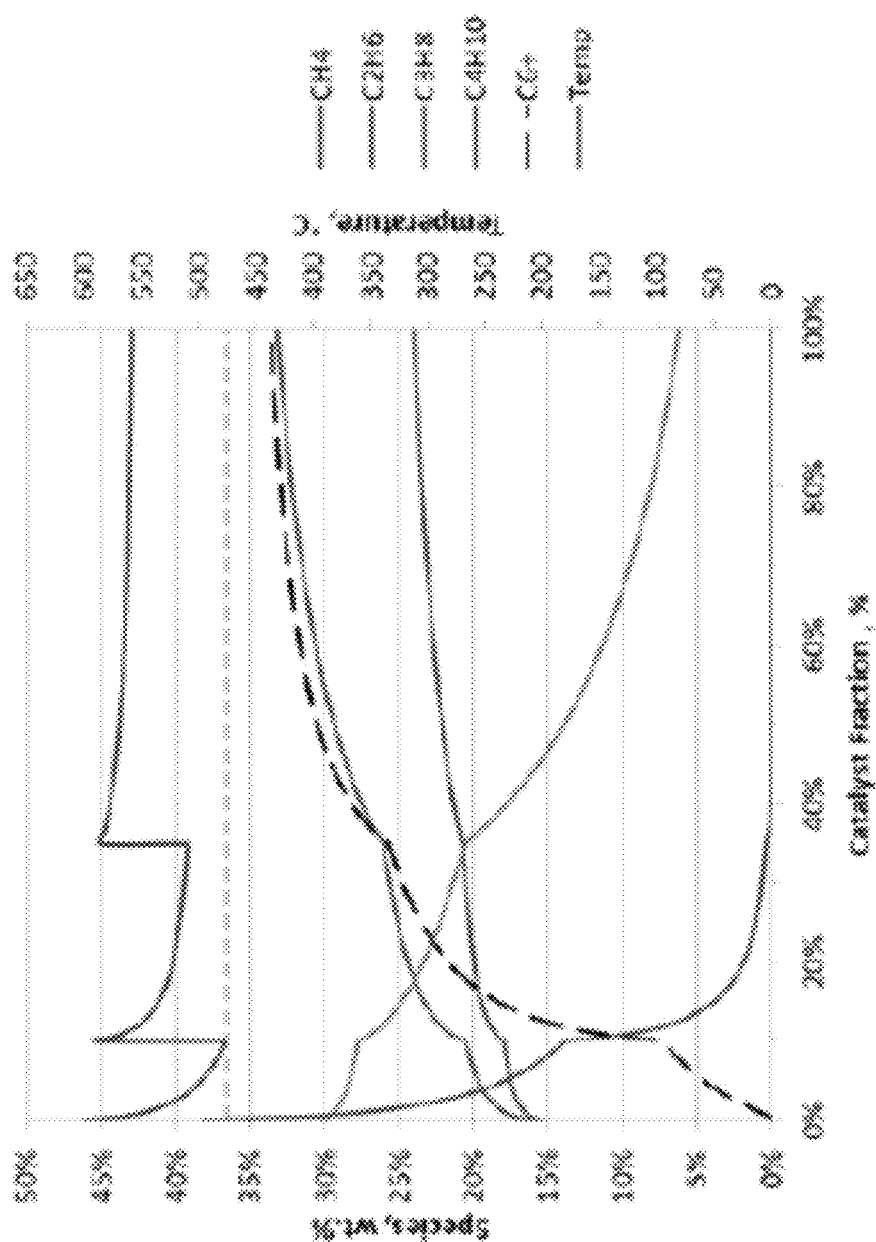
FIG. 5 shows modeled results for performance of fixed bed radial flow reactors for conversion of gas phase products to liquid products.

A reactor train containing three fixed bed radial flow reactors was modeled during conversion of a $C_3$ and $C_4$ enriched natural gas feed to form (aromatic) liquid products. The modeling was performed using a kinetic model developed from laboratory experiments. The modeled catalyst was a self-bound Ga-promoted H-ZSM-5 catalyst. The catalyst particle size relative to the dimensions of the radial flow reactors satisfied the relationships shown in Equations (1) and (2) with values of A=200, B=300, C=50, and D=150. The catalyst was distributed between the reactors so that 10 wt % of the catalyst was in the first reactor, 25 wt % was in the second reactor, and the remaining 65 wt % was in the third reactor. FIG. 5 shows results from the modeling of the conversion reaction.

As shown in FIG. 5 based on the right-hand axis, the initial temperature for the feed was between 600° C. and 610° C. After the first reactor, the temperature dropped to about 475° C., which was the largest temperature drop. After the second reactor, the temperature dropped to about 520° C., while the third reactor finished at close to 550° C. After the first reactor and second reactor, the partially converted feed was heated again to a temperature between 600° C. and 610° C. The reaction pressure during the model run was approximated as being roughly constant at about 400 kPa. This demonstrates the using multiple fixed bed radial-flow reactors can allow for control of temperature within a desired temperature range. In particular, the reactor train of fixed bed radial-flow reactors allowed for control of the temperature between 475° C. and 625° C., with a majority of the catalyst being exposed to the feed at a temperature within a few degrees of 550° C.

As shown in FIG. 5 based on the left-hand axis, the initial feed included about 38 wt % butane, about 30 wt % propane, and about 15 wt % each of methane and ethane. A portion of the $C_4$ components were converted in the first reactor (10% of catalyst), while conversion of the $C_4$ components was substantially complete after the second reactor (35% catalyst). Between 5 wt % and 10 wt % of the propane remained unconverted at the end of the reactor train. The modeling results in FIG. 5 show that substantially complete conversion of a paraffin-containing feed could be achieved under the reaction conditions. It is noted that ethane and methane are not reactive under the conversion conditions. Instead, the conversion conditions result in a small amount of additional production of methane and ethane.

Example 2—Modeling of Pressure During Conversion Reaction

The kinetic model used in Example 1 was also used to compare the pressure drop between using fixed bed radial flow reactors and conventional fixed bed axial flow (such as trickle bed) reactors. In these simulations, the model feed used in Example 1 was exposed to an equivalent amount of catalyst in either a radial flow or an axial flow configuration. For the axial flow simulations within the model, the catalyst was modeled as a single catalyst bed, although the results would not change within the model if the catalyst was split among multiple axial flow beds. The catalyst for the radial flow simulations was split among three reactors in the manner described in Example 1.

Figure 6:
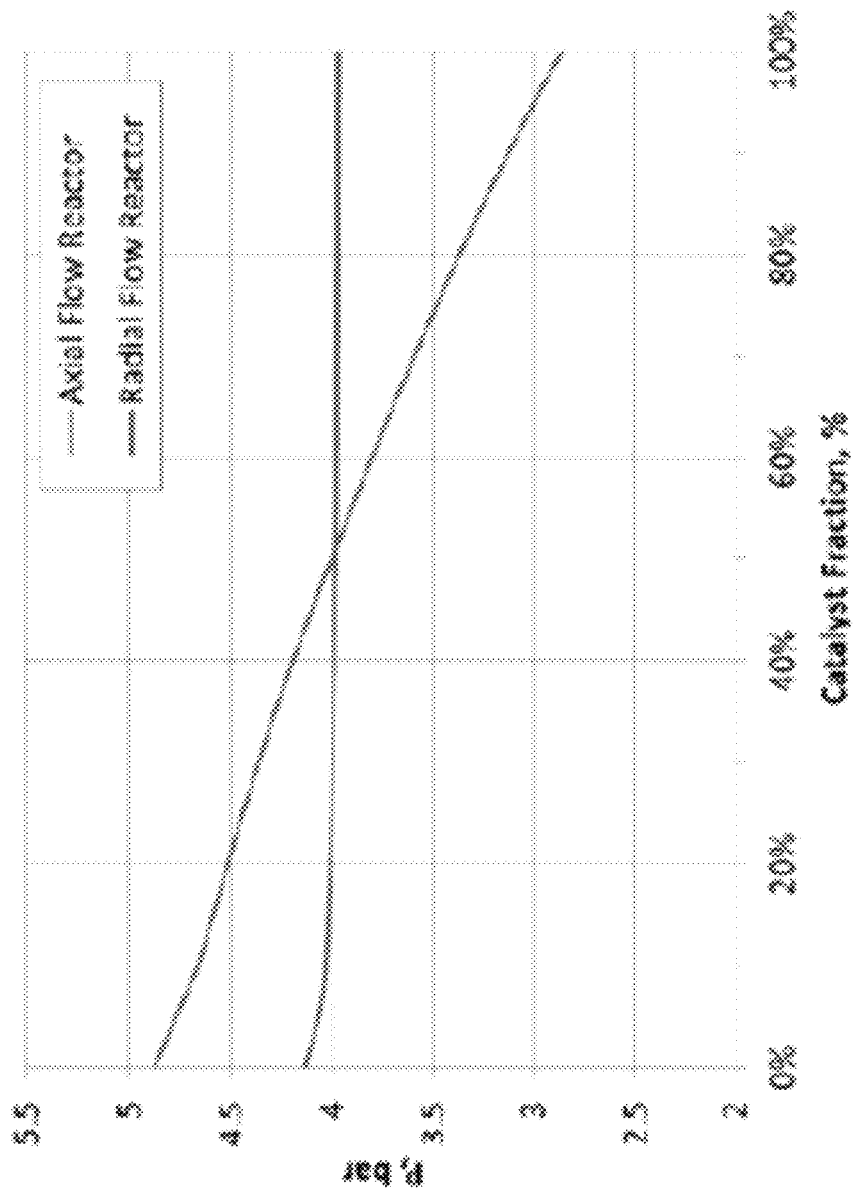
FIG. 6 shows modeled results for performance of axial flow and radial flow reactors for conversion of gas phase products to liquid products.

The reaction was modeled under isothermal conditions, so that a temperature of 550° C. was maintained throughout each type of reactor. FIG. 6 shows the pressure profile for the radial flow catalyst beds and the axial flow catalyst bed. For the radial flow configuration, a small initial pressure drop was observed of less than 20 kPag (0.2 barg), with little or no pressure drop across the remaining portion of the catalyst during radial flow. By contrast, under axial flow conditions, the pressure drop between the beginning and the end of the catalyst bed was roughly 200 kPag (2 barg). In order to achieve an average pressure of roughly 400 kPa-a, this required initially pressurizing the feed to a pressure of about 480 kPa-a, so that the final effluent pressure was about 280 kPa-a. It is noted that in an actual reaction system, subsequent processing components in a reaction system would also typically have minimum pressure requirements, so that any additional loss of pressure due to non-modeled effects (such as pressure drops through valves) could pose additional difficulties. Based on the results in FIG. 6, use of a fixed bed axial flow reactor would require some type of intermediate compression (or multiple stages of intermediate compression) to achieve a similar pressure profile to the relatively constant pressure profile of a fixed bed radial-flow reactor train.

Example 3—Catalyst Preparation

The invention will now be more particularly described with reference to the following Examples. Numerous modifications and variations are possible and it is to be understood that within the scope of the appended claims, the invention may be practiced otherwise than as specifically described herein.

The alpha value is a measure of the cracking activity of a catalyst and is described in U.S. Pat. No. 3,354,078 and in the Journal of Catalysis, Vol. 4, p. 527 (1965); Vol. 6, p. 278 (1966) and Vol. 61, p. 395 (1980), each incorporated herein by reference. The experimental conditions of the test used herein included a constant temperature of 538° C. and a variable flow rate as described in detail in the Journal of Catalysis, Vol. 61, p. 395 (1980).

H-ZSM-5 was used as the starting material to synthesize the catalysts of the Examples. As used in the Examples, the percentages of metal, i.e., gallium (Ga), zinc (Zn), and phosphorous (P), are in weight percent, which is based on the weight of the catalyst. Metal addition to H-ZSM-5 extrudate containing a binder was completed by conventional incipient wetness techniques. Zinc nitrate and gallium nitrate were used as precursors for metal addition. Solutions of the nitrate salt were prepared by dissolving the appropriate amount of metal salt into deionized water. The solution volume required for incipient wetness impregnation was determined using the absorption factor for the catalyst (g H$_2$O/g catalyst). The metal salt solution was then distributed over the aluminosilicate and left at ambient conditions for 1 hour, followed by drying at 250° F. (121° C.) for 6 hours in flowing air (5 vol. air/vol. solids/min.). The resulting solids were then treated at 1000° F. (538° C.) for 3 hours in flowing air (5 vol. air/vol. solids/min.). Table 2 shows the properties of the catalysts that were tested.

TABLE 1

| Sample | Metal Loading (wt. %) | Wt. % Aluminosilicate (Zeolite) | Wt. % Binder | Alpha Value (prior to metal addition) |
|---|---|---|---|---|
| A | 1.5% Ga | 100 | None | 460 |
| B | 1.5% Ga | 65 | 35% silica | 670 |
| C | 1.5% Ga | 65 | 35% alumina | 430 |
| D | 1.5% Ga | 80 | 20% alumina | 1200 |
| E | 3% Zn | 100 | None | 460 |
| F | 3% Zn | 65 | 35% silica | 670 |
| G | 3% Zn | 80 | 20% alumina | 1200 |
| H | 1.5% Zn | 100 | None | 460 |
| I | 1.5% Zn | 65 | 35% alumina | 430 |
| J | 1.5% Zn/1% P | 65 | 35% alumina | 430 |
| K | 1% Zn | 100 | None | 460 |
| L | 1% Zn/1% P | 100 | None | 460 |

Additional Embodiments

Embodiment 1. A fixed bed radial flow reactor, comprising: an outer annular volume defined by an interior of a reactor wall and an exterior of a gas-permeable catalyst bed wall, the interior of the reactor wall defining an outer annular radius R1; a central volume defined by the interior of a gas-permeable central column wall and a column cap, the interior of the central column wall defining a column radius R3; an inner annular volume defined by an interior of the catalyst bed wall, an exterior of the central column wall, an inner annular top, and an inner annular bottom, the interior of the catalyst bed wall defining an inner annular radius R2, the inner annular volume comprising a catalyst bed, the inner annular volume being in direct fluid communication with the outer annular volume through the catalyst bed wall, the inner annular volume being in direct fluid communication with the central volume through the central column; a plurality of catalyst particles in the catalyst bed, the catalyst particles comprising an equivalent particle diameter $d_{P,e}$; and a first reactor opening and a second reactor opening, the first reactor opening being in fluid communication with the outer annular volume, the second reactor opening being in fluid communication with the central volume, wherein the outer annular radius R1, inner annular radius R2, and the equivalent particle diameter $d_{P,e}$ satisfy the relationship $C^*d_{P,e} \leq R1-R2 \leq D^*d_{P,e}$, where C is at least 30 and D is 300 or less, and wherein the inner annular radius R2, the column radius R3, and the equivalent particle diameter $d_{P,e}$ satisfy the relationship $A^*d_{P,e} \leq R2-R3 \leq B^*d_{P,e}$, where A is at least 100 and B is 600 or less.

Embodiment 2. The reactor of Embodiment 1, wherein the first reactor opening comprises a reactor inlet, or wherein the second reactor opening comprises a reactor outlet, or a combination thereof.

Embodiment 3. The reactor of any of the above embodiments, wherein the inner annular volume further comprises gas phase hydrocarbons, at least 5 vol % of the gas phase hydrocarbons comprising $C_{3+}$ paraffins relative to a weight of the gas phase hydrocarbons, the at least 5 vol % of $C_{3+}$ paraffins optionally comprising at least 5 vol % of $C_3$-$C_6$ paraffins or $C_3$-$C_4$ paraffins.

Embodiment 4. The reactor of any of the above embodiments, wherein the catalyst bed wall comprises a perforated wall, a catalyst bed screen, or a combination thereof.

Embodiment 5. A method for processing a paraffin-containing feed, comprising: exposing a feed comprising about 30 vol % to about 70 vol % of $C_{3+}$ paraffins to one or more fixed beds of a conversion catalyst to form a conversion effluent comprising $C_6$-$C_{12}$ aromatics (or $C_6$-$C_9$ aromatics), the one or more fixed beds of the conversion catalyst comprising fixed beds in one or more radial flow reactors, a combined pressure drop across the one or more fixed beds being less than about 100 kPag (or less than about 50 kPag), the one or more radial flow reactors comprising: an outer annular volume defined by an interior of a reactor wall and an exterior of a gas-permeable wall, the interior of the reactor wall defining an outer annular radius R1; a central volume defined by the interior of a central column and a column cap, the interior of the central column defining a column radius R3; and an inner annular volume defined by an interior of the gas-permeable wall, an exterior of the central column, an inner annular top, and an inner annular bottom, the interior of the gas-permeable wall defining an inner annular radius R2, the inner annular volume comprising a catalyst bed, the inner annular volume being in direct fluid communication with the outer annular volume through the gas-permeable wall, the inner annular volume being in direct fluid communication with the central volume through the central column, wherein the conversion catalyst comprises catalyst particles comprising an equivalent particle diameter $d_{P,e}$, wherein the outer annular radius R1, inner annular radius R2, and the equivalent particle diameter $d_{P,e}$ satisfy the relationship $C^*d_{P,e} \leq R1-R2 \leq D^*d_{P,e}$, where C is at least 30 and D is 300 or less, and wherein the inner annular radius R2, the column radius R3, and the equivalent particle diameter $d_{P,e}$ satisfy the relationship $A^*d_{P,e} \leq R2-R3 \leq B^*d_{P,e}$, where A is at least 100 and B is 600 or less.

Embodiment 6. The method of Embodiment 5, wherein the feed is exposed to the conversion catalyst at a temperature of about 450° C. to about 650° C. (or about 475° C. to about 625° C.), a pressure in the one or more fixed catalyst beds comprising at least about 200 kPa-a (or at least about 300 kPa-a, or about 200 kPa-a to about 450 kPa-a), and a WHSV of about 0.1 $hr^{-1}$ to about 4.0 $hr^{-1}$ (or about 0.5 $hr^{-1}$ to about 2.0 $hr^{-1}$).

Embodiment 7. The method of Embodiment 5 or 6, the method further comprising heating at least a portion of the feed after exposure of the feed to a first catalyst bed of the one or more catalyst beds and prior to exposure of the feed to a second catalyst bed of the one or more catalyst beds.

Embodiment 8. The method of any of Embodiments 5-7, wherein a temperature drop across a first catalyst bed of the one or more catalyst beds is about 125° C. or less, or about 100° C. or less.

Embodiment 9. The method of any of Embodiments 5-8, further comprising: separating $C_{3+}$ paraffins from a natural gas feedstock to form at least a fraction comprising $C_{3+}$ paraffins; mixing at least a portion of the fraction separated $C_{3+}$ paraffins with a gas comprising methane, ethane, or a combination thereof to form an enriched feedstock, wherein exposing the feed comprising about 30 vol % to about 70 vol % of $C_{3+}$ paraffins to one or more fixed beds of conversion catalyst comprises exposing at least a portion of the enriched feedstock to the one or more fixed beds of conversion catalyst, the gas comprising methane, ethane, or a combination thereof optionally comprising a portion of the natural gas feedstock, a fraction separated from the natural gas feedstock, or a combination thereof.

Embodiment 10. The method of any of Embodiments 5-9, wherein the about 30 vol % to about 70 vol % $C_{3+}$ paraffins comprise about 30 vol % to about 70 vol % of $C_3$-$C_6$ paraffins or $C_3$-$C_4$ paraffins.

Embodiment 11. The method of any of Embodiments 5-10, further comprising separating the conversion effluent to form a fraction comprising $C_6$-$C_{12}$ aromatics (or $C_6$-$C_9$ aromatics), and combining at least a portion of the fraction comprising $C_6$-$C_{12}$ aromatics with a hydrocarbon liquid.

Embodiment 12. The reactor or method of any of the above embodiments, a) wherein A is at least 170, or at least 200, or at least 300, or wherein B is 560 or less, or 500 or less, or 400 or less, or a combination thereof; or b) wherein C is at least 50, or wherein D is less than 200, or less than 150, or c) a combination of a) and b).

Embodiment 13. The reactor or method of any of the above embodiments, wherein the equivalent particle diameter is about 0.2 cm to about 4.0 cm, or about 1.0 cm to about 3.0 cm.

Embodiment 14. The reactor of any of the above embodiments, wherein i) the catalyst particles comprise at least one medium pore molecular sieve having a Constraint Index of 2-12; ii) the catalyst particles comprise ZSM-5, ZSM-11, ZSM-12, ZSM-22, ZSM-23, ZSM-35, ZSM-48, MCM-22, MCM-49, or a combination thereof; iii) the catalyst particles comprise 0.1 wt % to 5.0 wt % of a metal from Groups 3-13 of the periodic table relative to a weight of the catalyst particles, the metal optionally comprising Ga, In, or a combination thereof; or d) a combination of a) and/or b) and/or c).

Embodiment 15. A conversion effluent comprising $C_6$-$C_9$ aromatics made according to the reactor or method of any of the above embodiments.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method for processing a paraffin-containing feed, comprising:
   exposing a feed comprising about 30 vol % to about 70 vol % of $C_3$-$C_4$ paraffins to one or more fixed beds of a conversion catalyst to form a conversion effluent comprising $C_6$-$C_{12}$ aromatics, the one or more fixed beds of the conversion catalyst comprising fixed beds in one or more radial flow reactors, a combined pressure drop across the one or more fixed beds being less than about 100 kPag, the one or more radial flow reactors comprising:
   an outer annular volume defined by an interior of a reactor wall and an exterior of a gas-permeable wall, the interior of the reactor wall defining an outer annular radius R1;
   a central volume defined by the interior of a central column and a column cap, the interior of the central column defining a column radius R3; and
   an inner annular volume defined by an interior of the gas-permeable wall, an exterior of the central column, an inner annular top, and an inner annular bottom, the interior of the gas-permeable wall defining an inner annular radius R2, the inner annular volume comprising a catalyst bed, the inner annular volume being in direct fluid communication with the outer annular volume through the gas-permeable wall, the inner annular volume being in direct fluid communication with the central volume through the central column, wherein the conversion catalyst comprises catalyst particles comprising an equivalent particle diameter $d_{P,e}$;

wherein the outer annular radius R1, inner annular radius R2, and the equivalent particle diameter $d_{P,e}$ satisfy the relationship $$C*d_{P,e} \leq R1-R2 \leq D*d_{P,e}$$

where C is at least 30 and D is 300 or less, and wherein the inner annular radius R2, the column radius R3, and the equivalent particle diameter $d_{P,e}$ satisfy the relationship $$A*d_{P,e} \leq R2-R3 \leq B*d_{P,e}$$

where A is at least 100 and B is 600 or less.

2. The method of claim 1, wherein the feed is exposed to the conversion catalyst at a temperature of about 450° C. to about 650° C., a pressure in the one or more fixed catalyst beds comprising at least about 200 kPa-a, and a WHSV of about 0.1 hr$^{-1}$ to about 4.0 hr$^{-1}$.

3. The method of claim 1, the method further comprising heating at least a portion of the feed after exposure of the feed to a first catalyst bed of the one or more catalyst beds and prior to exposure of the feed to a second catalyst bed of the one or more catalyst beds.

4. The method of claim 1, wherein a temperature drop across a first catalyst bed of the one or more catalyst beds is about 125° C. or less.

5. The method of claim 1, further comprising:

separating $C_3$-$C_4$ paraffins from a natural gas feedstock to form at least a fraction comprising $C_3$-$C_4$ paraffins;

mixing at least a portion of the fraction separated $C_3$-$C_4$ paraffins with a gas comprising methane, ethane, or a combination thereof to form an enriched feedstock, wherein exposing the feed comprising about 30 vol % to about 70 vol % of $C_3$-$C_4$ paraffins to one or more fixed beds of conversion catalyst comprises exposing at least a portion of the enriched feedstock to the one or more fixed beds of conversion catalyst.

6. The method of claim 5, wherein the gas comprising methane, ethane, or a combination thereof comprises a portion of the natural gas feedstock, a fraction separated from the natural gas feedstock, or a combination thereof.

7. The method of claim 1, further comprising separating the conversion effluent to form a fraction comprising $C_6$-$C_{12}$ aromatics or $C_6$-$C_9$ aromatics, and combining at least a portion of the fraction comprising $C_6$-$C_{12}$ aromatics with a hydrocarbon liquid.

8. The method of claim 1, wherein A is at least 300, or wherein B is 400 or less, or a combination thereof, or wherein C is at least 50, or wherein D is less than 150, or a combination of any two or more thereof, or a combination of all thereof.

9. The method of claim 1, wherein the equivalent particle diameter is about 0.2 cm to about 4.0 cm.

10. The method of claim 1, wherein the catalyst particles comprise ZSM-5, ZSM-11, ZSM-12, ZSM-22, ZSM-23, ZSM-35, ZSM-48, MCM-22, MCM-49, or a combination thereof.

11. The method of claim 1, wherein the catalyst particles comprise 0.1 wt % to 5.0 wt % of a metal from Groups 3-13 of the periodic table relative to a weight of the catalyst particles.

12. The method of claim 11, wherein the metal comprises Ga, In, or a combination thereof.

* * * * *